(12) United States Patent
Guitteaud et al.

(10) Patent No.: US 9,185,196 B2
(45) Date of Patent: Nov. 10, 2015

(54) METHOD FOR DETERMINING GAZE DIRECTION AND DEVICE FOR SAME

(75) Inventors: Eric Clément Guitteaud, Paris (FR); Pierre Youri Bascoulergue, Paris (FR)

(73) Assignee: MATCHIC LABS (FR)

( * ) Notice: Subject to any disclaimer, the term of this patent is extended or adjusted under 35 U.S.C. 154(b) by 164 days.

(21) Appl. No.: 13/979,877

(22) PCT Filed: Jan. 10, 2012

(86) PCT No.: PCT/FR2012/050065
§ 371 (c)(1),
(2), (4) Date: Jul. 16, 2013

(87) PCT Pub. No.: WO2012/098325
PCT Pub. Date: Jul. 26, 2012

(65) Prior Publication Data
US 2013/0295994 A1    Nov. 7, 2013

(30) Foreign Application Priority Data

Jan. 19, 2011    (FR) ...................... 11 50405

(51) Int. Cl.
| G06K 9/00 | (2006.01) |
|---|---|
| H04M 1/02 | (2006.01) |
| F16M 13/00 | (2006.01) |
| F16M 13/04 | (2006.01) |
| G06F 3/01 | (2006.01) |
| A61B 3/113 | (2006.01) |

(52) U.S. Cl.
CPC ............ *H04M 1/0264* (2013.01); *F16M 13/00* (2013.01); *F16M 13/04* (2013.01); *G06F 3/013* (2013.01); *G06K 9/00604* (2013.01); *A61B 3/113* (2013.01)

(58) Field of Classification Search
CPC ............ G02B 27/017; G02B 27/0093; G02B 2027/0138; G02B 2027/0187; G02B 2027/0136; G06F 3/013; G06F 3/011; G06F 3/015; G06F 3/016; G06F 3/017; A61B 3/113; A61B 3/158; H04N 5/235; H04N 13/0484; H04N 13/0468
See application file for complete search history.

(56) References Cited

U.S. PATENT DOCUMENTS

| 4,836,670 A | 6/1989 | Hutchinson |
| 5,583,795 A * | 12/1996 | Smyth ........................ 702/150 |

(Continued)

FOREIGN PATENT DOCUMENTS

| FR | 2 937 428 A1 | 4/2010 |
| GB | 2 467 301 | 7/2010 |

OTHER PUBLICATIONS

International Search Report and Written Opinion dated Jun. 14, 2013 issued in corresponding International patent application No. PCT/FR2012/050065.

*Primary Examiner* — Ali Bayat
(74) *Attorney, Agent, or Firm* — Ostrolenk Faber LLP

(57) ABSTRACT

A device for supporting, in motion, a mobile terminal having a display surface, including a supporting element forming a hand grip for the device; and a plate mounted such that it can move in relation to the supporting element, the plate forming a housing receives mobile terminal in the use position, in which the display surface can be observed by a user. The device also has a plurality of reference light sources linked to the supporting element, which can emit light towards the user's eye and which are disposed in the environment of the housing in a two-dimensional array, the array being coplanar with the display surface of the mobile terminal that is intended to be received in the housing.

21 Claims, 6 Drawing Sheets

(56) References Cited

U.S. PATENT DOCUMENTS

| | | | |
|---|---|---|---|
| 5,621,457 A * | 4/1997 | Ishiwaka et al. | 348/78 |
| 7,401,920 B1 * | 7/2008 | Kranz et al. | 351/210 |
| 2002/0013573 A1 | 1/2002 | Telfair et al. | |
| 2003/0156257 A1 * | 8/2003 | Levola | 351/210 |
| 2005/0175218 A1 | 8/2005 | Vertegaal et al. | |
| 2010/0025444 A1 | 2/2010 | Tipton et al. | |
| 2010/0053555 A1 | 3/2010 | Enriquez et al. | |

* cited by examiner

Page 1 of US 9,185,196 B2

METHOD FOR DETERMINING GAZE DIRECTION AND DEVICE FOR SAME

CROSS-REFERENCE TO RELATED APPLICATIONS

The present application is a 35 U.S.C. §371 National Phase conversion of PCT/FR2012/050065, filed Jan. 10, 2012, which claims benefit of French Application No. 1150405, filed Jan. 19, 2011, the disclosures of which are incorporated herein by reference. The PCT International Application was published in the French language.

BACKGROUND OF THE INVENTION

1. Technical Field

The present invention relates to the field of the technologies associated with the measurement and the tracking of the direction of gaze (known as "eyetracking") and relates, more particularly, according to a first of its aspects, to a method for tracking the gaze of a user on a display surface observed by the user, consisting notably of the screen of a mobile terminal such as a mobile telephone or a touch-screen tablet, allowing it to be determined, while mobile, at which locations on the observed display surface the gaze of the user is aimed.

2. Related Art

By way of non-exclusive example of an application of the invention may notably be mentioned the analysis of the interactions of the gaze with a user interface, undertaken in the framework of behavioral studies aimed for example at evaluating areas of interest within this interface or at adapting the ergonomic properties of this interface.

In the prior art, two large families of eyetracking systems are distinguished:
  non-intrusive and non-portable systems;
  intrusive and portable systems.

All these systems use a basic technical principle consisting in evaluating the direction of gaze starting from the relative position of the corneal reflection of a light source and of the pupil.

The principle consists in disposing an LED (light-emitting diode) as a light source emitting radiation in the infrared wavelengths right next to the objective lens of a video camera intended to acquire images of the eye. This infrared LED emits light toward the eye in the same direction as the axis of the objective lens of the video camera. This light is reflected on the cornea of the eye: a light spot, called "Purkinje spot", then appears on the image of the cornea of the eye captured by the video camera.

The non-intrusive tracking system is a system which allows the movements of the eye to be recorded and hence the gaze to be tracked when the subject is for example looking at a computer screen.

This type of system is generally composed of a very high definition camera disposed at around sixty centimeters from the head of the user in the axis of the gaze of the subject.

Since this camera is high definition, it is then possible to distinguish the face of the user toward whom it is pointing. Then, by image processing and shape recognition, it is possible to identify the location of the eyes and to enlarge the image in order to accurately determine the position of the pupil with respect to the Purkinje spot. This system does not interact with the user, and the latter does not have to wear special glasses or a helmet.

However, the main drawback of this system is that it relies on the use of a high-definition camera whose cost exceeds by more than 100 times the price of a camera with standard resolution. In addition, during the analysis of the gaze, the user cannot move his/her head beyond a three-dimensional limit defined by the angle of view of the camera which is filming the eye.

Furthermore, the screen that the user is watching must necessarily be fixed, which constitutes an important limitation, preventing this type of system from being adapted to display screens of mobile terminals such as mobile telephones or touch-screen tablets for example, which, by their nature, are used while moving.

Intrusive eyetracking systems allow this eyetracking to be recorded when the user is looking at a global scene such as the cockpit of an aircraft for example or else the dashboard of a car.

This type of system is generally composed of a first video camera disposed at around ten centimeters from the head of the user in the axis of gaze of the user. This video camera is close to the head, and it must therefore be fixed to a special pair of glasses or to a helmet.

Since this video camera is directly filming the area of the eye, by image processing, it is possible to accurately recognize the position of the pupil with respect to the Purkinje point.

Thus, this system endows the user with a great freedom of movement. The user can thus move around while at the same time affording the camera the possibility of analyzing the direction of his/her gaze. In addition, such a system allows the use of all types of cameras having a reduced cost compared for example with high-definition cameras.

This type of system also comprises a second video camera, referred to as a 'scene camera', for filming the scene observed by the user. The two video streams respectively generated by the first video camera and by the second video camera are processed in order to produce a single video stream representing the scene and including a cursor allowing the locations in the scene where the user directs his/her gaze to be tracked at each moment in time. Such a system is well known to those skilled in the art, notably by the example given in the document US 2010/0053555.

However, one drawback of this system resides in the fact that the first video camera used to determine the position of the eye and the second video camera allowing the scene observed by the user to be filmed are in the same reference frame, which is linked to the reference frame of the head of the user. Moreover, this system is not well adapted to tracking the gaze over the surface of a mobile object, and, more particularly, over the display screen of a mobile terminal, such as a mobile telephone, in a context of mobility. Indeed, when the scene camera records a scene where the user is in the process of looking, while moving around, at the screen of a mobile telephone for example, the object in question being watched and filmed becomes mobile in the stream of video images resulting from the recording of the scene by the scene camera. It is then particularly difficult to be able to automatically determine what the user, while moving around, is looking at.

For example, if the user is continuously looking at an area of interest on the screen of the mobile telephone in a context of mobility, the point of gaze of the user does not move according to said area of interest but, on the stream of video images resulting from the recording of the scene by the scene camera, it moves around according to the position in the image of the area of interest being watched, itself mobile within the resulting video stream.

Accordingly, within this context of mobility, it is not possible to readily, and especially automatically, determine that the user is continuously looking at the area of interest in question, except, which is not desirable, by endowing the system with powerful image processing and shape recognition means, capable of accurately recognizing the area of interest in question within the stream of video images, in order to deduce from this that the point of gaze on the image really has followed this area of interest, mobile within the image.

In this context, the aim of the invention is to overcome the drawbacks of the prior art and, in particular, to solve the problems encountered by the known eyetracking systems of the intrusive and portable type in order to be able to readily and automatically determine, within a context of mobility, the direction of gaze with respect to an object being watched, notably a mobile telephone.

SUMMARY OF THE INVENTION

According to a first of its aspects, the invention therefore relates to a method for tracking the gaze of a user over a display surface of a mobile terminal being observed by the user, consisting in determining the position of the gaze of the user on the display surface being observed, in which is provided a first video camera situated in the axis of the gaze of the user and a first light source directed toward the eye and situated near to the objective lens of the first video camera, for collecting a first video signal comprising at least the image of the pupil and that of the corneal reflection of the first light source, a second video signal is collected comprising images of the display surface being observed by the user, the first video signal is analyzed for measuring, in the reference frame of the eye, the direction of gaze as a function of the position of the center of the pupil with respect to the center of the corneal reflection of the first light source and a cursor is displayed in the second video signal representing the position of the gaze on the display surface being observed as a function of the direction of gaze measured in the reference frame of the eye.

According to the invention, the second video signal is captured in a reference frame distinct from the reference frame of the first video camera, linked to that of the display surface being observed, a plurality of reference light sources are positioned in the reference frame of capture of the second video signal directed toward the eye and disposed according to a two-dimensional array coplanar with the display surface being observed, such that the first video signal collected by the first video camera furthermore comprises the image of the corneal reflections of the reference light sources on the eye and in that the first video signal is analyzed so as to supply the position of the center of the corneal reflections of the reference light sources on the eye and the position of the gaze in the plane of the display surface being observed is determined based on the position of the center of the corneal reflections of the reference light sources on the eye and on the direction of gaze measured in the reference frame of the eye.

Advantageously, in the reference frame of the eye, based on the position of the center of the corneal reflections of the reference light sources on the eye, the position of the gaze is determined with respect to the position of the surface being observed on the eye and a conversion relationship is used between a system of coordinates linked to the reference frame of the eye and a system of coordinates linked to the plane formed by the plurality of reference light sources corresponding to the plane of the display surface being observed in order to determine the position of the gaze in the plane of the display surface being observed as a function of the position of the gaze determined in the reference frame of the eye.

According to one embodiment, an initial operation is carried out for calibration of the positioning of the surface being observed in the reference frame of capture of the second video signal as a function of the eye of the user, consisting in calculating the position of the center of the pupil on each of the mounting points of a predefined test pattern positioned in the plane of the surface being observed allowing points of correspondence between the plane of the surface being observed and the image of the eye to be defined.

Preferably, a second light source is provided directed toward the eye near to the objective lens of the first video camera designed to enhance the illumination of the eye, in particular in the case of an implementation of the system in a dark environment.

Preferably, a second video camera is provided positioned in the reference frame of the display surface being observed for capturing the second video signal.

According to one variant, the second video signal is captured by using a video output of the mobile terminal.

The invention also relates, according to another of its aspects, to a device for supporting, in a mobile state, a mobile terminal having a display surface, notably a mobile telephone or a similar object, for the implementation of the method according to the invention, characterized in that it comprises a supporting element forming a manual gripping mechanism for the device and a tray installed to be mobile with respect to the supporting element, the tray forming an accommodation designed to receive the mobile terminal in a position of use in which the display surface is able to be observed by a user, the device comprising a plurality of reference light sources linked to the supporting element, capable of emitting light toward the user and disposed in the environment of the accommodation according to a two-dimensional array coplanar with the display surface of the mobile terminal intended to be received in the accommodation.

According to one embodiment, the device comprises a first support frame designed to support the plurality of reference light sources, the first support frame being composed of a plurality of arms mounted on the supporting element at a respective first end of each of them and on a respective second end of which one respective light source from the plurality of reference light sources is mounted.

Advantageously, the device can furthermore comprise a video camera, referred to as second video camera, attached to the supporting element and capable of being oriented toward the accommodation designed to receive the mobile terminal in order to capture images of the display surface being observed.

According to one embodiment, the device comprises a second support frame designed to support the second video camera, comprising an arm attached by a first end to the supporting element, and extending from this first end to a second end positioned above the accommodation designed to receive the mobile terminal, this second end of the arm being equipped with means for fixing the video camera capable of holding the video camera in the correct orientation.

Advantageously, the plurality of reference light sources is composed of four light-emitting diodes non-aligned when they are taken in threes.

Preferably, the light-emitting diodes emit radiation in the infrared wavelength range.

Preferably, the tray is mounted in rotation on the supporting element between two positions substantially at a right angle to each other, in such a manner as to respectively define a position referred to as portrait and a position referred to as landscape for the display surface of the mobile terminal intended to be received in the accommodation and means for locking the tray are provided in each of these respective positions.

The invention also relates, according to yet another of its aspects, to a system for tracking the gaze of a user over a display surface of a mobile terminal in a mobile state, characterized in that it comprises a device for supporting said mobile terminal according to the invention, a portable unit of equipment attached to the user comprising a support designed to be adjusted to the head of the user and an arm mounted onto the support and carrying at its distal end a video camera, referred to as first video camera, in the axis of gaze of the user, and a first light source directed toward the eye and situated near to the objective lens of the first video camera, and a processing unit comprising a first video input interface capable of receiving a first video signal captured by the first video camera of the portable equipment comprising the image of the pupil, that of the corneal reflection of the first light source directed toward the eye and that of the corneal reflections corresponding to each of the reference light sources equipping the device for supporting the object, a second video input interface capable of receiving a second video signal comprising the image of the display surface being observed by the user, and a processor module capable of measuring, from the first video signal, the direction of gaze in the reference frame of the eye as a function of the position of the center of the pupil with respect to the center of the corneal reflection of the first light source and of determining the position of the gaze in the plane of the display surface being observed, based on the position of the center of the corneal reflections of the reference light sources in the first video signal and on the direction of gaze measured in the reference frame of the eye.

Preferably, the device for supporting the mobile terminal implemented in the system according to the invention comprises a video camera, referred to as second video camera, for supplying the second video signal, said second video camera can advantageously be attached to the supporting element and being capable of being oriented toward the accommodation designed to receive the mobile terminal for capturing images of the display surface being observed, and the second video input interface of the processing unit is connected to a video output of this second video camera which supplies the second video signal.

According to one variant, the second video input interface of the processing unit is connected to a video output of the mobile terminal capable of supplying the second video signal.

Advantageously, the processing unit comprises a video output interface capable of supplying the second video signal in which the images of the display surface being observed display a cursor representing the position of the gaze in the plane of the surface being observed determined by the processor module.

Preferably, the system comprises a module for synchronizing the illumination of the first light source and of the reference light sources with the capture of the video signal by the first video camera of the portable equipment, said synchronization module comprising a video input interface capable of receiving the first video signal from the first video camera of the portable equipment, power supply means designed to control in a synchronous manner the illumination and the extinction of the first light source and of the reference light sources and means for processing the video signal configured with said power supply means so as to control the illumination of the first light source and of the reference light sources at the rate of one image in two with respect to the images captured by the first video camera of the portable equipment.

Advantageously, the arm mounted on the support of the portable equipment is a telescopic arm equipped with anti-rotation means for maintaining the first video camera in the correct orientation.

In one embodiment, the telescopic arm comprises two linked sliding parallel rods, at least one of which has a sliding control at the proximal end of the arm.

Preferably, the support of the portable equipment is a spectacle frame with two branches, the arms being fixed onto one of the branches of the frame.

Preferably, the arms mounted on the support of the portable equipment carry a second light source directed toward the eye near to the objective lens of the first video camera, designed to promote the illumination of the eye.

BRIEF DESCRIPTION OF THE DRAWINGS

Other features and advantages of the invention will become apparent upon reading the description presented hereinafter of one particular embodiment of the invention, given by way of non-limiting example, with reference to the appended drawings in which.

DESCRIPTION OF PREFERRED EMBODIMENTS

The system which will now be described by way of example is designed to determine the instantaneous position of the direction of gaze of a human subject, hereinafter the user, relative to a display surface being observed of an object, in particular taking the form of a display screen of a mobile terminal, such as a mobile telephone or a touch-screen tablet for example. The invention is applicable in a context of use of the object by the user in a real mobile situation. Accordingly, in the system of the invention, it is provided for the object, which is normally held in the hand by the user when it is being used, to be mobile with respect to the head of the user.

As has been previously explained, the known eyetracking systems of the intrusive and portable type are not adapted to recording a scene where the user is looking at an object in a context of real mobility, since the object being watched and filmed becomes mobile in the video resulting from the recording of the scene by the scene camera. Accordingly, while still coming within the family of eyetracking systems of the intrusive and portable type, the system of the invention provides the capture of the scene observed by the user, in other words typically the screen of the mobile telephone, in the reference frame of the mobile telephone, and the positioning within this same reference frame of the reference light sources designed to be reflected in the eye of the user, these sources being furthermore disposed relative to the mobile telephone in the same plane as that formed by the screen of the mobile telephone.

Thus, the image of the display surface being observed (the screen) will always be located at the same place in the video resulting from the scene camera and the reflections of the reference light sources will allow, after calculation, as will be seen hereinbelow, the position of the gaze deduced from the position of the pupil in the image of the eye to be linked to the position of the gaze in the reference frame of the observed scene.

Figure 1:
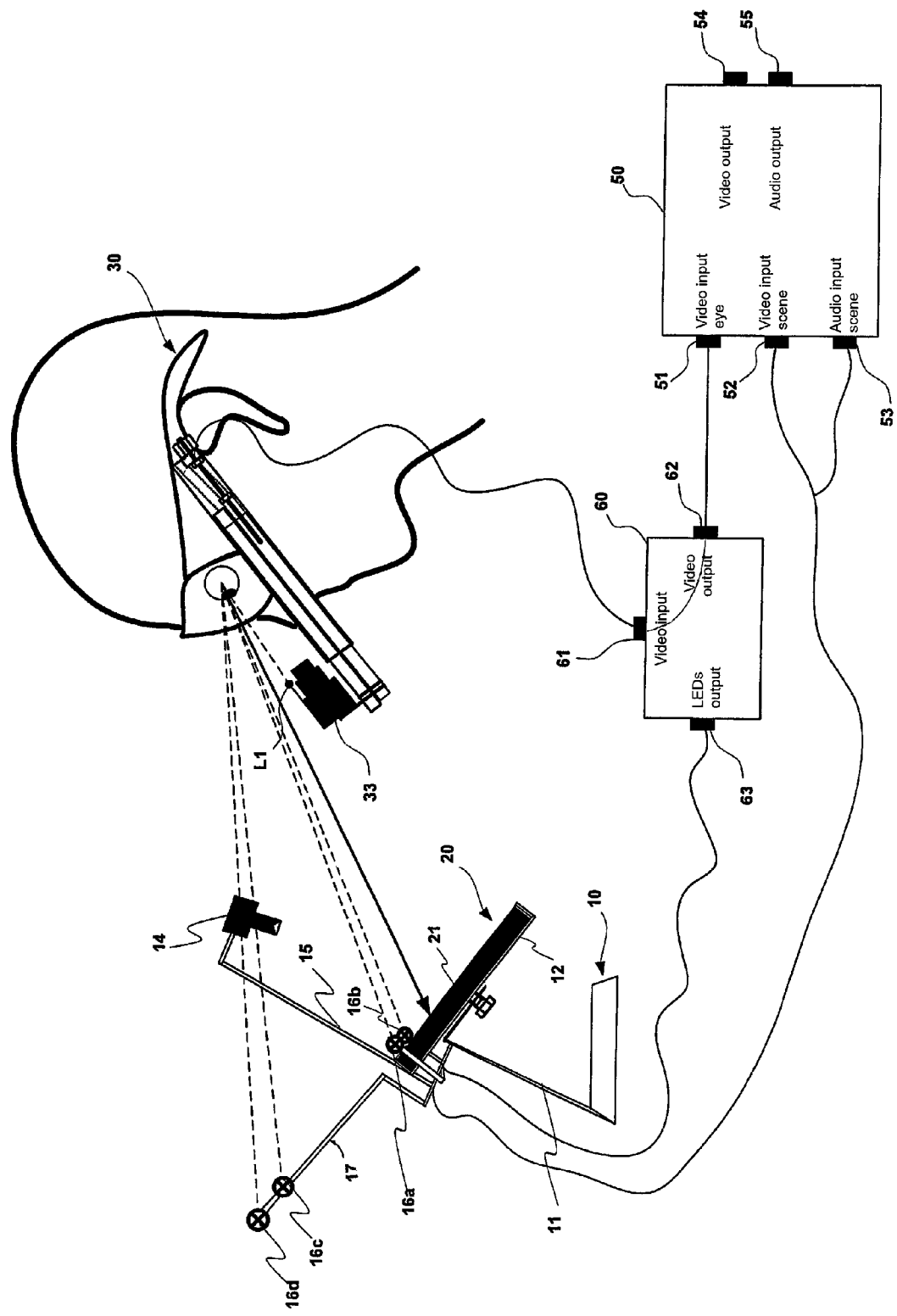
FIG. 1 shows an overall view of the eyetracking system according to the invention.
Figure 2:
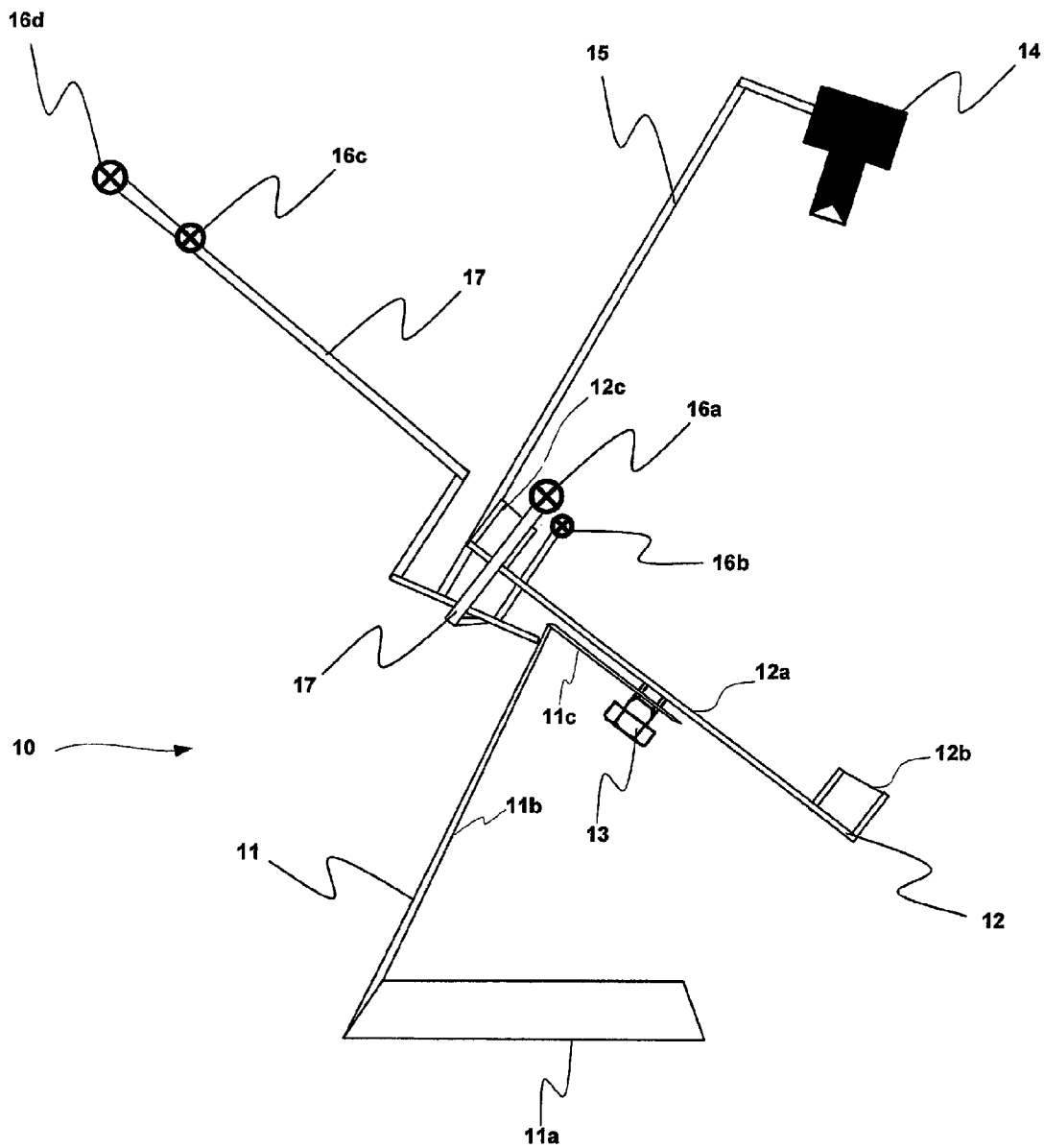
FIG. 2 illustrates schematically a side view of the device according to the invention for supporting, in a mobile state, the object observed by the user.
Figure 3:
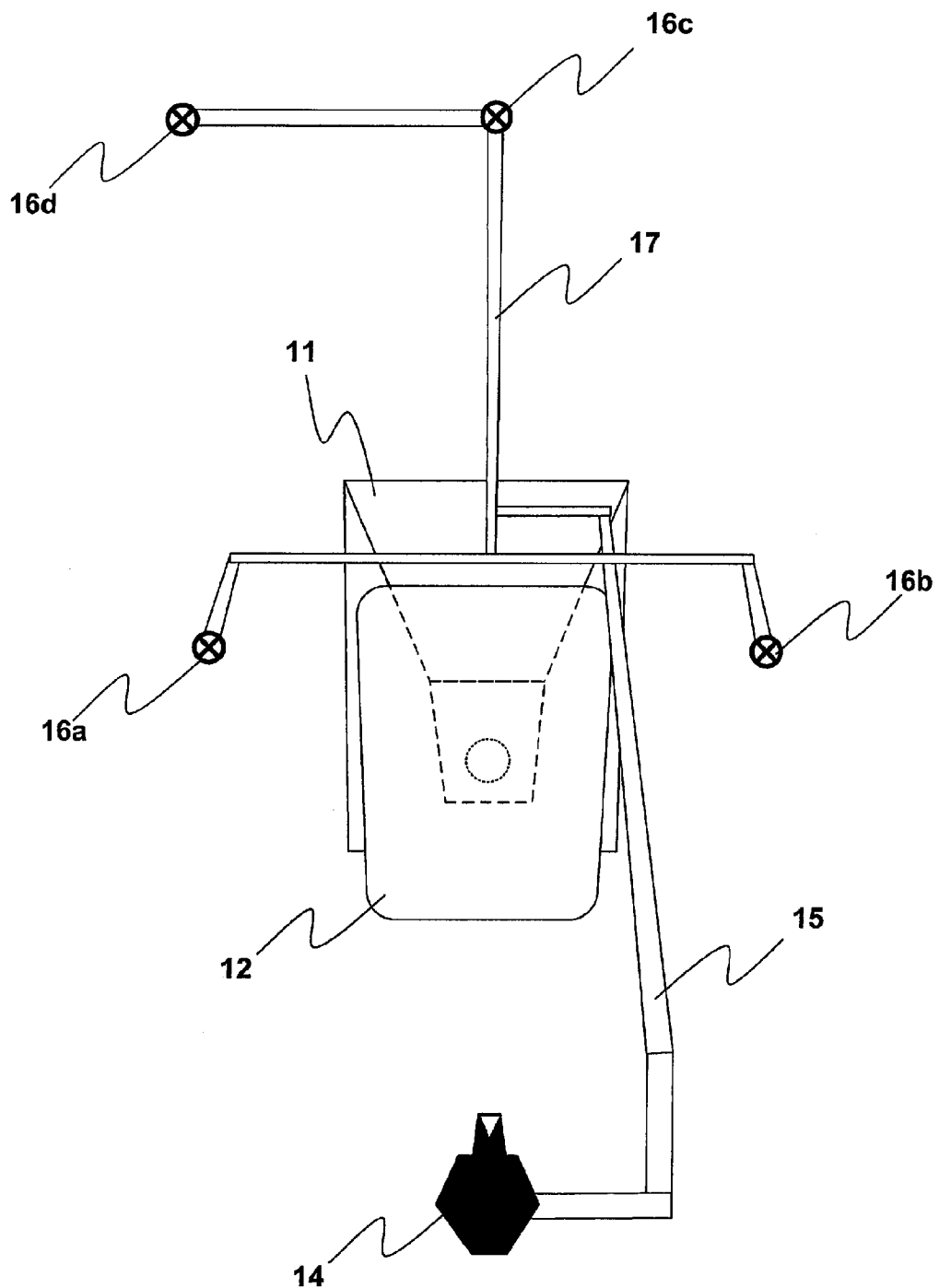
FIG. 3 illustrates a top view of the device in FIG. 2.

For this purpose, the embodiment of the system according to the invention illustrated in FIG. 1 shows a device 10 for supporting, in a mobile state, a mobile terminal 20 having a display surface 21 designed to be watched by the user. The mobile terminal for example consists of a mobile telephone and the display surface consists of the screen of the mobile telephone. The device 10, illustrated more precisely in FIGS. 2 and 3, comprises a supporting element 11 designed, on the one hand, to be used as a base plate for the device and, on the other hand, to be used as a manual gripping mechanism for the device. It takes the form of a single bulk piece constructed as a first part 11a forming a plane support, a second part 11b running from the plane support and forming a handle allowing the user to hold and maneuver the whole assembly, and a third part 11c, running in an inclined manner from one end of the part 11b forming a handle and onto which a tray 12 is mounted. The tray 12 comprises a plane surface 12a fitted for example with a lower and upper end stop 12b and 12c thus bounding an accommodation designed to receive the mobile telephone in a position of use, i.e. in a position in which the display screen is capable of being observed by the user, notably when he/she is holding the device in one hand. The tray 12 is designed to be installed to be mobile on the supporting element 11 and, more precisely, is mounted in rotation on the inclined part 11c of the supporting element. The tray 12 is for example fitted with a locking screw 13, allowing the tray 12 to be locked onto the inclined part 11c of the supporting element 11 in well-defined positions. The screw 13 allows the tray 12 for example to be locked in two positions substantially at a right angle to each other, in such a manner as to respectively define a position referred to as portrait and a position referred to as landscape for the display screen of the mobile telephone intended to be received in the accommodation.

The device 10 furthermore comprises a video camera 14, referred to as scene camera, provided for capturing images of the screen of the mobile telephone received in the accommodation, in the same reference frame as that of the mobile telephone. In order to achieve this, the scene camera 14 is held above the tray 12 forming accommodation for the mobile telephone by a light frame 15 equipping the device, which is attached to the supporting element 11, preferably in an upper region of the part 11b forming a handle, so as not to interfere with the gripping of the whole assembly. This support frame 15 designed to support the scene camera 14 in the reference frame of the mobile telephone received in the accommodation of the device 10 comprises for example an arm fixed by a first of its ends to the supporting element 11 and extending from this first end toward a second end positioned above the tray forming an accommodation. This second end of the arm is equipped with means for fixing the scene camera 14, not shown, allowing the scene camera 14 to be held in the correct orientation. Thanks to this arrangement, the scene camera 14 provided for filming the screen of the mobile telephone received in the accommodation of the device 10 is fixed with respect to the mobile telephone in the reference frame of the mobile telephone itself. In addition, the screen being watched and filmed will remain fixed in the video resulting from the capture of the screen by the scene camera 14, including in a context of mobility where, for example, the user moves his/her head with respect to the screen being watched or else moves the mobile telephone in space at the same time as he/she is looking at the screen.

According to one variant embodiment, the video signal from the screen observed by the user may be captured by directly using the video output of the mobile terminal, in the case where the mobile terminal is equipped with such a video output conventionally allowing the screen of the mobile terminal to be displayed on an external display medium (television or computer screen for example). According to this variant embodiment, the presence of a scene camera equipping the device 10 as explained hereinabove is not necessary.

Moreover, in order to be able to determine while in motion at which locations on the screen the gaze of the user is aimed, the device comprises a plurality of reference light sources 16a, 16b, 16c, 16d, which are therefore positioned in the same reference frame as that of the mobile telephone received in the accommodation and which are provided in order to emit light toward the user that is intended to be reflected on the eye of the user. The reference light sources 16a, 16b, 16c, 16d are preferably composed of four light-emitting diodes (LEDs) emitting radiation in the infrared wavelengths. The four infrared LEDs are more precisely disposed in the environment of the accommodation according to a two-dimensional array situated in the same plane as that formed by the screen of the mobile telephone received in the accommodation and furthermore exhibit the feature of not being aligned when taken in threes. The plane formed by the four infrared LEDs 16a to 16d is disposed parallel to the plane formed by the plane surface 12a of the tray 12 forming an accommodation for the mobile telephone, and is situated slightly above the latter, at a height taking into account the thickness of the object received in the accommodation, in such a manner that the four LEDs are positioned in the same plane as that formed by the screen of the object.

The four reference infrared LEDs are held around the tray 12 forming an accommodation for receiving the mobile telephone by a light support frame 17 equipping the device and which is attached to the supporting element 11, preferably in the same area of the supporting element 11 from which the light frame 15 for supporting the scene camera 14 is deployed. This support frame 17 for the four infrared LEDs is for example composed of four arms, each having a free end to which is attached an infrared LED in such a manner that the latter emits light toward the eye of the user, the other end of each of the arms of the support frame 17 being attached to the supporting element 11 of the device. The arms of the support frame are arranged with respect to one another in such a manner as to satisfy the geometrical positioning constraints for the infrared LEDs such a described hereinabove.

The embodiment of the system according to the invention illustrated in FIG. 1 also shows a device 30 of the intrusive and portable type for the identification of the position of the eye with respect to a light spot reflected on the cornea called "Purkinje spot". This equipment, which is designed to be attached to the user, is described more precisely in FIGS. 4 and 5. It comprises a support 30 designed to be adjusted to the head of the user. Here, the support 30 takes the form of a frame of a pair of glasses with the corrective lenses removed, and comprises two branches 31, at least one of which is sufficiently wide at least in its frontal region for laterally receiving an arm 32 which is used to rigidly fix a miniature video camera 33 to the glasses frame 30. As will be seen in detail in the following part, the length of the arms is adjustable by a mechanism using a worm screw 36.

The arm 32 is composed of a plate with an elongated base 34, fixed for example by adhesive bonding to the glasses frame branch 31 and extending the latter toward the front. Two parallel tubes 35a, 35b are fixed by any means, for example by ribbons of adhesive, to the support plate 34 and serve as guiding members with two sliding rods 36a, 36b which for example take the form of thin tubes. The distal ends of the two rods 36a, 36b, protrude from the tubes 35a, 35b and are attached to one another by means 36c, for example by clamp rings with an interposed strut, or else by rivets passing through the assembly of the two tubes. Again at the distal end, the same means 36c, or other means 33a, may be used for fixing the video camera 33 to the rods 36a, 36b, in a fixed orientation, substantially in the axis of the gaze of the user. At the proximal end, the ends of the rods 36a, 36b also protrude from the outer tubes 35a, 35b. The assembly of the two rods 36a, 36b can therefore slide without rotating in the tubes 35a, 35b. A single rod could also be provided having a non-cylindrical cross section in order to guarantee the absence of rotation, but the present embodiment has the advantage of allowing a very smooth sliding movement and of only requiring very common and low cost commercially available elements.

At its proximal end, the plate 34 receives an L-shaped axial guide 38 comprising a smooth axial passage aligned with the axis of the tube 35b and of the rod 36b. This passage receives the threaded rod 40 of a worm screw. An end-stop nut 39 is screwed on and blocked, for example by adhesive bonding, onto the threaded rod 40, in the neighborhood of the axial guiding part 38, whereas an adjustment thumb-wheel 37 is bonded to the proximal end of the screw, whose axial movement is thus limited by the end-stop cooperation of the elements 37, 38 and 39, whereas its free rotation is possible by operating the adjustment thumb-wheel. The threaded rod 40 engages in a nut 41 fixed, for example by adhesive bonding, to the proximal end of the rod 10b.

The operation of the equipment is as follows. The glasses frame is adjusted on the head of the user, potentially following a pre-adjustment as mentioned hereinabove. The fine adjustment of the sharpness of the images captured by the camera 33 is carried out by the user by means of the thumb-wheel 37:

Rotating the thumb-wheel 37 in a first predefined direction makes the element 41 come closer to the element 38. However, the elements 41, 36c, 35a, 35b, and 33 are rigidly fixed together, hence the camera comes closer to the eye of the user.

Rotating the thumb-wheel in the direction opposite to the first predefined direction makes the element 41 move further away from the element 38. However, the elements 41, 36c, 35a, 35b, and 33 are rigidly fixed together, hence the camera moves away from the eye of the user.

Figure 4:
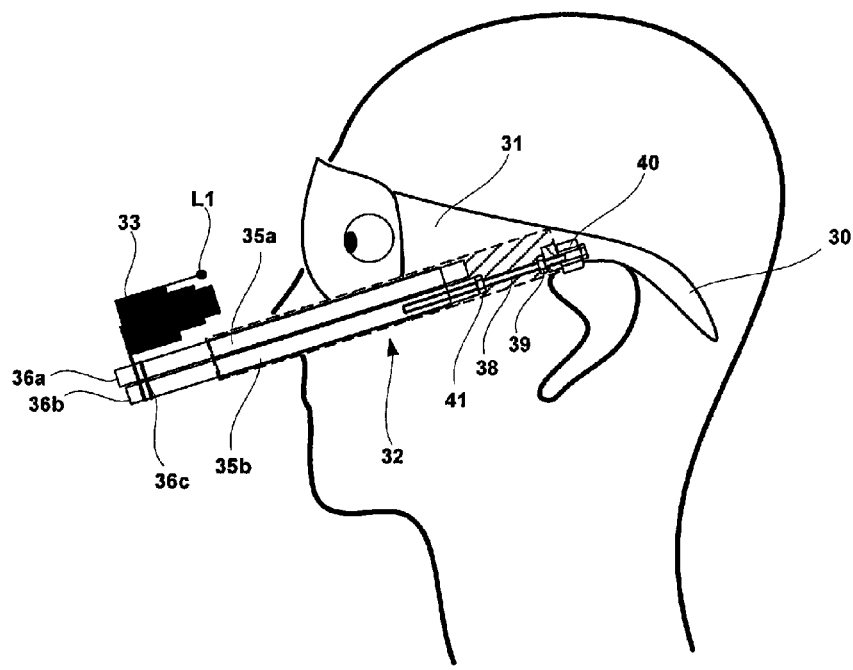
FIG. 4 illustrates schematically a profile view of the portable equipment designed to be carried by the user in the framework of the implementation of the eyetracking system according to the invention.
Figure 5:
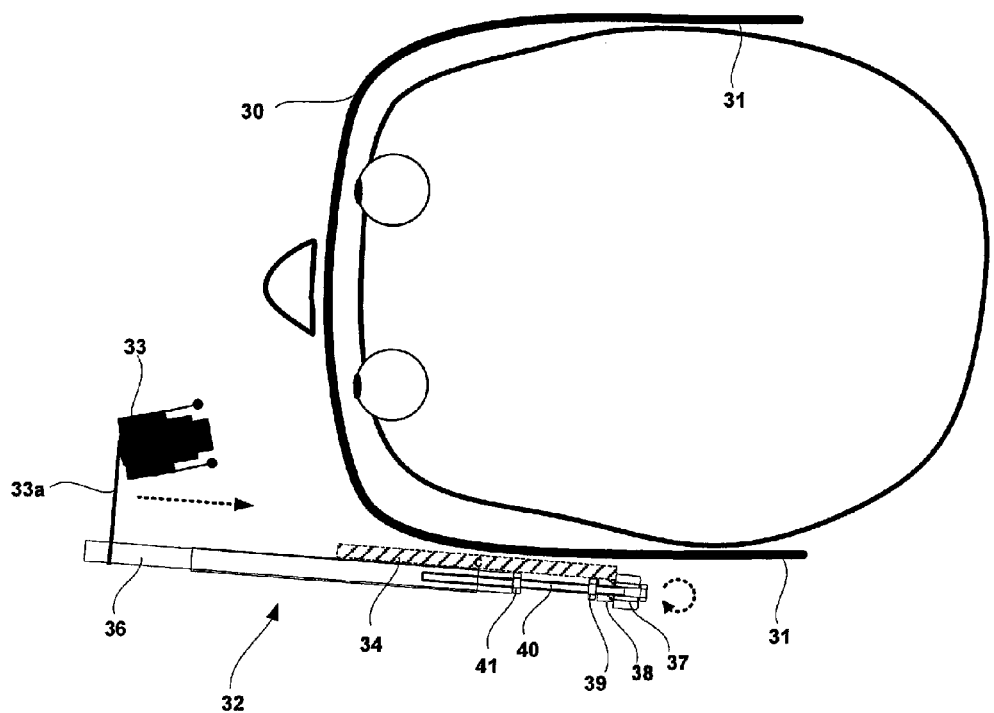
FIG. 5 illustrates a top view of the portable equipment in FIG. 4.

Thanks to this arrangement, bringing the camera 33 closer to or further away from the position of the eye of the user, and hence adjusting the focus, is easily carried out and with one hand by means of a simple rotation of the thumb-wheel 37 disposed at the proximal end of the arm 32, near to the ear, as indicated in FIG. 4, in other words in a location fixed with respect to the head of the subject where maneuvering the thumb-wheel does not risk moving the whole assembly of the device in an undesirable way, which does not therefore need to be held.

The equipment furthermore comprises a first light source L1 directed toward the eye and situated near to the objective lens of the video camera. It is for example fixed directly onto the body of the camera 33. This first light source is preferably composed of an LED emitting radiation in the infrared wavelengths, and which is henceforth referred to as "Purkinje" LED. Where necessary, a second light source L2, of the infrared LED type, could be added that is directed toward the eye and disposed near to the objective lens of the video camera, in the same manner as for the source L1, for the case of use of the system in particularly dark places.

The embodiment of the system according to the invention illustrated in FIG. 1 also shows a processing unit 50 comprising a first video input interface 51 for receiving the video signal captured by the video camera 33 of the portable equipment arranged on the user and a second video input interface 52 for receiving the video signal captured by the scene camera 14, together with an audio input interface 53, allowing the audio signal coming from the microphone equipping the scene camera to be received. The processing unit also comprises at least one video output interface 54 and one audio output interface 55.

Thus, when the scene camera 14 captures images of the screen of the mobile telephone disposed on the supporting device 10 and observed by the user, the images of the screen are transmitted to the processing unit 50 in the form of a video signal using a link connected to the video input interface 52 of the processing unit and are stored in suitable storage means of the processing unit. According to the variant embodiment described hereinabove without a scene camera, the video input interface 52 of the processing unit 50 is designed to be connected to the video output of the mobile terminal received in the accommodation of the device 10, whereas the audio input interface 53 can be connected to a separate microphone. In this variant, the video recording of the screen observed by the user is therefore supplied directly by the mobile terminal itself, via the video output from the mobile terminal.

Furthermore, when the video camera 33 of the portable equipment arranged on the head of the user captures images of the eye of the user, the images of the eye of the user are transmitted to the processing unit 50 in the form of a video signal using a link connected to the video input interface 51 of the processing unit and are stored in suitable storage means of the processing unit.

However, in one preferred embodiment, the system comprises an additional module 60 for synchronizing the illumination of the "Purkinje" LED and of the reference LEDs with the capture of the video signal by the video camera 33 of the portable equipment. This module is interposed between the video camera 33 and the processing unit 50; it comprises a video input interface 61 for receiving the video signal acquired by the camera 33 of the portable equipment and a video output interface 62. It also comprises means 63 for supplying power to the LEDs designed to control, in a synchronous manner, the illumination and the extinction of the "Purkinje" LED and of the reference LEDs.

Thus, according to this preferred embodiment, when the video camera 33 of the portable equipment adjusted on the head of the user captures images of the eye of the user, the images of the eye are transmitted to the synchronization module 60 in the form of a video signal using a link connected to the video input interface 61 of the synchronization module, and are stored in suitable storage means of the synchronization module for processing. In parallel with the processing of the video signal by the synchronization module, this video signal is re-transmitted to the processing unit 50 using a link connecting the video output interface 62 of the synchronization module to the video input interface 51 of the processing unit 50, without modification and such as it has been received at the video input interface 61.

The role of the synchronization module 60 is to detect a synchronization signal contained in the video signal received and to control the illumination of the "Purkinje" LED and of the reference LEDs as a function of this synchronization signal, in such a manner as to synchronize the illumination of these LEDs with the capture of an image. More particularly, the four reference LEDs 16a to 16d and the "Purkinje" LED L1 are controlled by the synchronization module so as to flash in a synchronous manner at the rate of one image in two with respect to the images of the eye captured by the camera 33 of the portable equipment. The term 'synchronous' is taken to mean the fact that, when the video signal is recorded by the camera 33 of the portable equipment, the LEDs will for example be ON during the recording of the odd-numbered images, whereas they will be OFF during the recording of even-numbered images. Indeed, the fact that the LEDs are ON for one image in two only will allow the effective position of the light reflections of the LEDs in the resulting image of the eye to be better discriminated.

More precisely, according to one embodiment, the synchronization module uses electronic components in order to extract from the video signal of the camera 33 a first information relating to the even- and odd-numbered frame synchronization cue of this video signal and to process this information based on the detection of a second information extracted from the video signal relating to the even- and odd-numbered image cue returned by the video signal. It is recalled that an image is composed of two frames (an odd-numbered frame and an even-numbered frame) and that a video stream is composed of a succession of images numbered from 1 to infinity comprising the group of odd-numbered images (numbered 1, 3, 5, etc.) and the group of even-numbered images (numbered 2, 4, 6, etc.). Therefore, when two images follow one another, one has an odd number and the other necessarily has an even number.

This processing of the video signal coming from the camera 33 may for example correspond to a calculation performed by the synchronization module on the basis of this information allowing the odd-numbered frame of the odd-numbered image to be identified in the video signal, so as to light the LEDs at the moment when the odd-numbered frame of the odd-numbered image is identified, which is equivalent to illuminating the scene of the odd-numbered frame that the camera is in the process of capturing. In this way, the duration of illumination of the LEDs is rigorously equal to the time of a single frame (i.e. the time of a half-image). Since the illumination of the LEDs is carried out over the duration of an odd-numbered frame only and starts at the beginning of a complete image, it is certain that the illumination will take place necessarily over one complete image and will not be able to overlap onto the following image. For this purpose, the synchronization module implements processing means capable of extracting a first piece of information relating to the even- and odd-numbered frame synchronization cue of this video signal, of processing this first information so as to obtain a second piece of information relating to the even- and odd-numbered image cue returned by the video signal and of performing an operation of the AND logic type between the odd-numbered frames and the odd-numbered images obtained in such a manner as to determine the command for illumination/extinction of the LEDs to be sent to the module supplying power to the LEDs.

It is to be noted that, as a variant, a digital camera can be used allowing the synchronization signal for the even- and odd-numbered images to be directly recovered. Indeed, such digital cameras advantageously make the image synchronization cue available without it being necessary to extract it from the video signal.

The synchronization module and its principle of operation are described in the patent document FR 2 937 428, to which the reader may usefully refer for further details.

Figure 6:
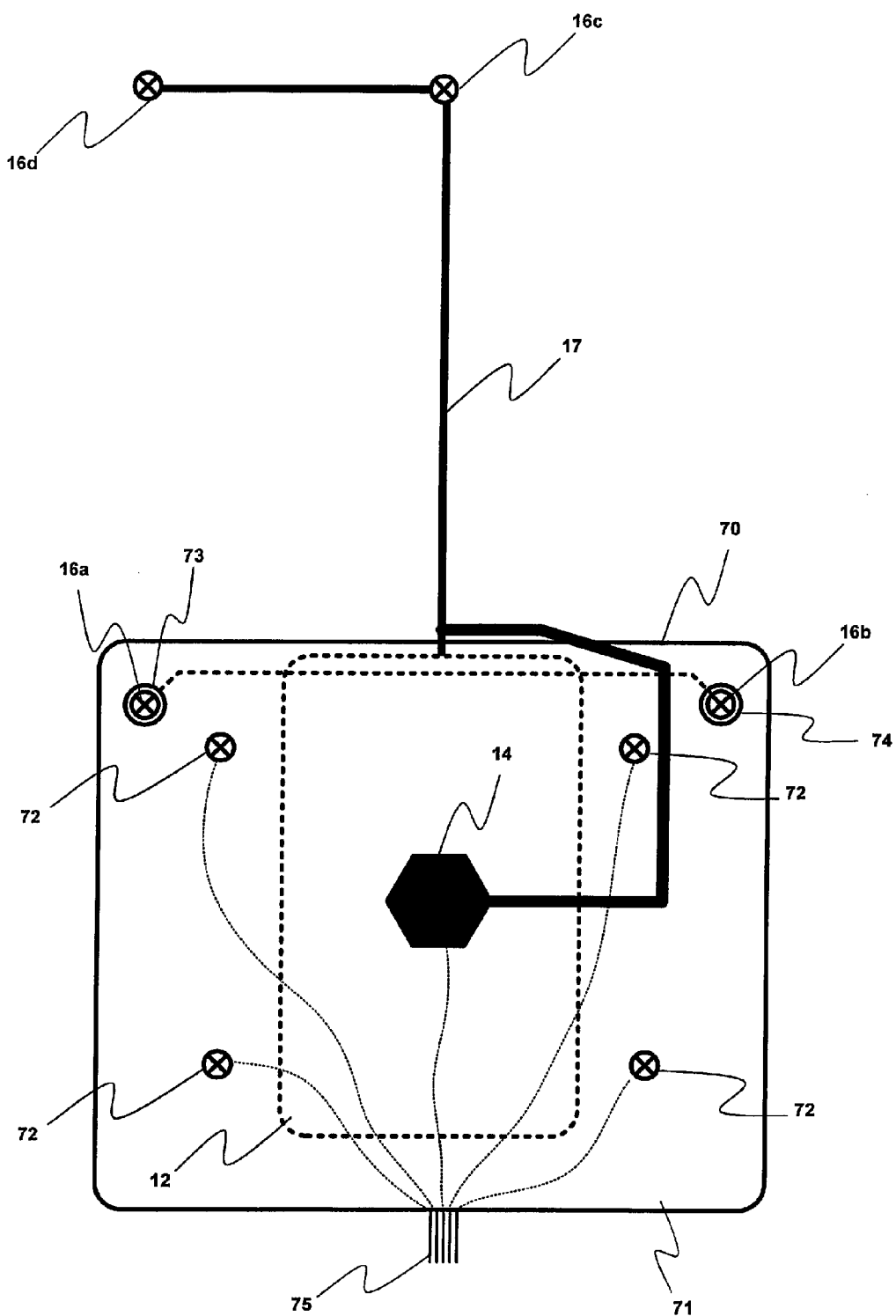
FIG. 6 illustrates a top view of the device in FIG. 2 on which a calibration test pattern has been disposed.

The operation of the system such as has just been described requires a calibration, on the one hand, of the intrinsic parameters of the eye of the user (each user in principle having a different eye) and of the positioning parameters of the tray 12 in the field of the scene camera 14. For this purpose, as illustrated in FIG. 6, a test pattern 70 is used positioned on the tray 12 of the device 10. The test pattern 70 takes the form of a plate 71 onto which five calibration LEDs 72 are fixed according to a predefined geometric shape and emit light toward the eye of the user, on which the portable equipment 30 has initially been adjusted. For example, four LEDs are disposed on the plate 71 so as to form a square and the fifth LED is disposed in the center of the square, the latter being masked by the camera 14 on the top view in FIG. 6. The calibration LEDs 72 used are LEDs of a color visible to the naked eye when they are lit, preferably a red color.

According to the example in FIG. 6, the plate 71 is has two holes 73, 74, through which the two reference LEDs 16a, 16b are passed when the plate 71 is positioned on the tray 12, such that, during the calibration operation, the plate 71 is perfectly centered with respect to the tray 12 and remains rigidly fixed to the latter.

The illumination of the five calibration LEDs 72 is carried out individually by means of a specific electronic command transmitted via a connection cable 75 connecting the calibration LEDs of the plate to a power supply control unit for the calibration LEDs not shown.

The calibration operation consists, more precisely, in gazing at the five flashing calibration LEDs one after the other. Using the image of the eye captured during the calibration operation, the various positions of the eye and corneal reflection spots are stored for each of the flashing calibration LEDs watched by the eye of the user. Subsequent to the storing of these various positions, the intrinsic parameters of the eye are calculated. Accordingly, it is now possible to determine a bijection between the direction of gaze, determined by a correlation of the position of the Purkinje spot and of the center of the pupil in the image of the eye, and the plane formed by the four reference LEDs 16a to 16d.

Figure 7:
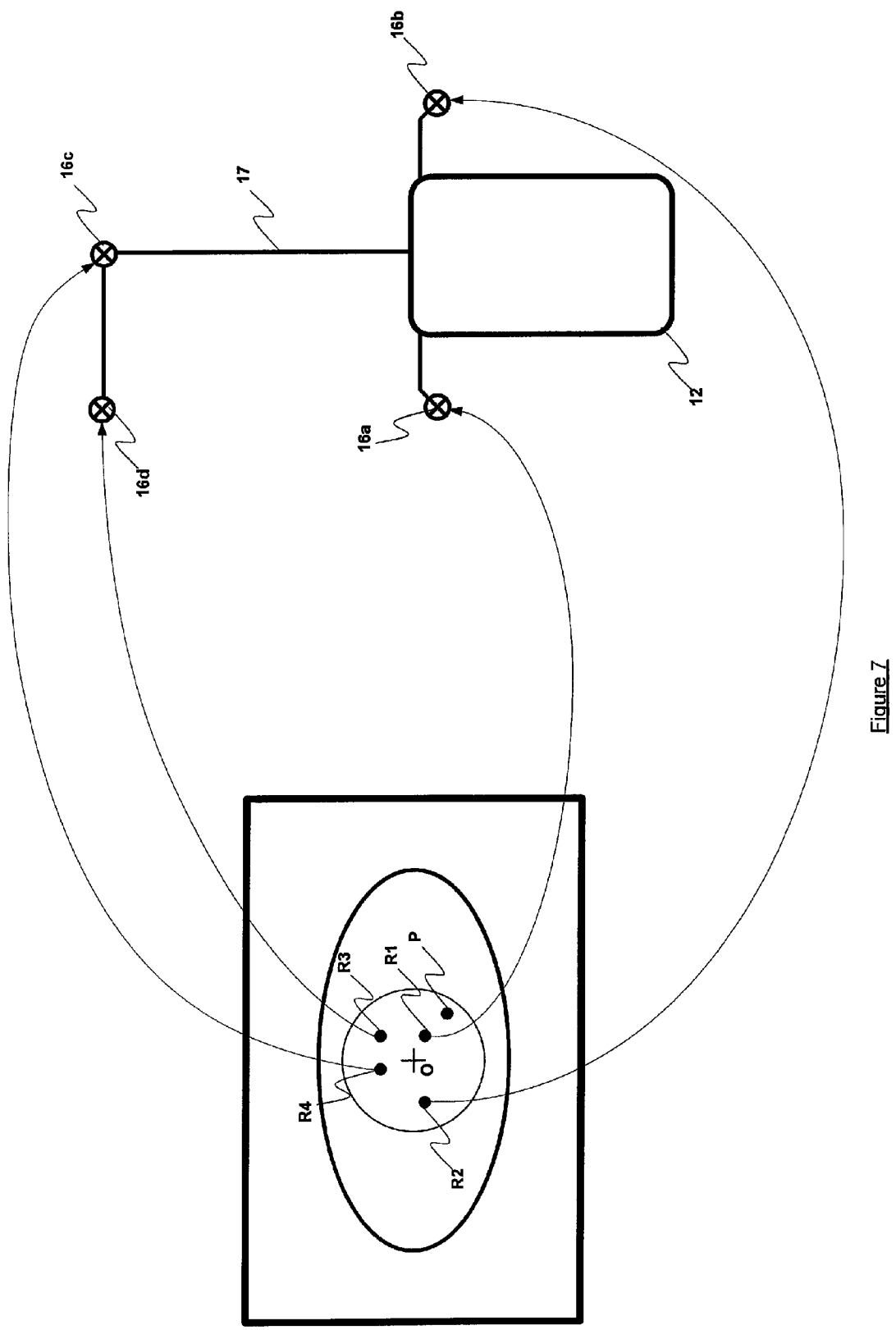
FIG. 7 illustrates an image of the eye captured by the camera of the portable equipment illustrated in FIGS. 4 and 5 when the system is in operation.

In operation, as has been previously explained, the four reference LEDs 16a to 16d of the device 10 for supporting, in a mobile state, the object being watched by the user and the "Purkinje" LED L1 of the portable equipment 30 adjusted on the head of the user flash in a synchronous manner at the rate of one image in two with respect to the images captured by the video camera 33 of the portable equipment 30. When the LEDs 16a to 16d and L1 are lit, they are reflected on the eye of the user and hence allow a fixed point in the captured image of the eye to be obtained by virtue of the corneal reflection. Thus, for two successively captured images, one of the two images contains the image of the corneal reflections of the lit LEDs, and the other image does not. A method for subtracting the two images with a processing by thresholding implemented by the processing unit 50 receiving the video signal coming from the camera 33 allows a resulting image to be obtained such as illustrated in FIG. 7, which only contains the image of the corneal reflections of the LEDs. Using special algorithms, the processing unit is capable of determining the position of the center of the pupil and that of the center of the corneal reflections in the image of the eye. From there, the position of the corneal reflection P of the "Purkinje" LED on the eye coming from the reflection of the "Purkinje" LED on the eye and the position of the center of the pupil O allow the direction of gaze, in other words the angle of gaze of the eye with respect to the scene being observed, to be determined in the reference frame of the eye. Accordingly, after calculation, the position in the image of the corneal reflections R1, R2, R3 and R4, respectively, of the four reference LEDs 16a, 16b, 16c and 16d, and the direction of gaze thus measured will allow an accurate determination of the position of the gaze on the surface being observed of the object disposed on the tray 12 of the supporting device 10.

Indeed, the determination of the position of the center of the corneal reflections of the four reference LEDs 16a to 16d in the image of the eye makes it possible to determine, in the reference frame of the eye, the position of the gaze with respect to that of the surface being observed on the surface of the eye. It is then possible, by a change of reference frame, to deduce from this the position of the gaze in the reference frame of the scene camera 14 which defines a plane formed by the four reference LEDs 16a to 16d corresponding to the plane of the surface being observed. The position of the gaze thus determined in the plane of the surface being observed is utilized in order to display in the scene video a cursor representing this position of the gaze. For this purpose, the processing unit applies a prior synchronization of the video signals coming respectively from the scene camera and from the video camera of the portable equipment in order to adjust the corresponding significant moments in time of these two video signals.

Thanks to the means of the invention, in particular the device for supporting the object in a mobile state, the image of the surface being observed will always be located at the same place in the scene video and the reference LEDs allow, after calculations, the position of the gaze of the user with respect to the image of the surface being observed to be determined. For this reason, maps of areas of interest on a user interface of a mobile telephone for example may be much more readily created since, over a given period of use of this mobile telephone in a context of real mobility, the user interface such as being watched and filmed will always be at the same location in the scene video and only the point of gaze will be mobile with respect to the image of the user interface.

What is claimed is:

1. A method for tracking the gaze of a user over a display surface of a mobile terminal observed by the user comprising the steps of:
determining a position of the gaze of the user on the display surface being observed, by using a first video camera situated in the axis of the gaze of the user and a first light source directed toward the eye and situated near to an objective lens of the first video camera, for collecting a first video signal comprising at least the image of a pupil of the user and that of a corneal reflection of the first light source, collecting a second video signal comprising images of the display surface, analyzing the first video signal for measuring in the reference frame of the eye the direction of gaze as a function of a position of the center of the pupil with respect to the center of the corneal reflection of the first light source, and displaying a cursor representing the position of the gaze on the display surface being observed in the second video signal as a function of the direction of gaze measured in the reference frame of the eye,
characterized in that the second video signal is captured in a reference frame distinct from the reference frame of the first video camera, linked to that of the display surface being observed, a plurality of reference light sources are positioned in the reference frame of capture of the second video signal directed toward the eye and disposed according to a two-dimensional array coplanar with the display surface being observed, such that the first video signal collected by the first video camera furthermore comprises the image of the corneal reflections of the reference light sources on the eye and in that the first video signal is analyzed so as to supply the position of the center of the corneal reflections of the reference light sources on the eye and the position of the gaze in a plane of the display surface being observed is determined based on the position of the center of the corneal reflections of the reference light sources on the eye and on the direction of gaze measured in the reference frame of the eye.

2. The method as claimed in claim 1, wherein in the reference frame of the eye, based on the position of the center of the corneal reflections of the reference light sources on the eye, the position of the gaze is determined with respect to the position of the surface being observed on the eye and a conversion relationship is used between a system of coordinates linked to the reference frame of the eye and a system of coordinates linked to the plane formed by the plurality of reference light sources corresponding to the plane of the display surface being observed in order to determine the position of the gaze in the plane of the display surface being observed as a function of the position of the gaze determined in the reference frame of the eye.

3. The method as claimed in claim 1, wherein an initial operation is carried out for calibration of the positioning of the surface being observed in the reference frame of capture of the second video signal as a function of the eye of the user, comprising calculating the position of the center of the pupil on each of the mounting points of a predefined test pattern positioned in the plane of the surface being observed allowing points of correspondence between the plane of the surface being observed and the image of the eye to be defined.

4. The method as claimed in claim 1, wherein a second light source is provided directed toward the eye near to the objective lens of the first video camera designed to promote the illumination of the eye.

5. The method as claimed in claim 1, wherein a second video camera is provided positioned in the reference frame of the display surface being observed in order to capture the second video signal.

6. The method as claimed in claim 1, wherein the second video signal is captured by using a video output of the mobile terminal.

7. A system for tracking the gaze of a user over a display surface of a mobile terminal in a mobile state, comprising
a device for supporting said mobile terminal having:
a supporting element forming a manual gripping mechanism for the device and a tray installed to be mobile with respect to the supporting element, the tray forming an accommodation designed to receive the mobile terminal in a position of use in which the display surface is able to be observed by a user, the device comprising a plurality of reference light sources linked to the supporting element, capable of emitting light toward the eye of the user and disposed in the environment of the accommodation according to a two-dimensional array coplanar with the display surface of the mobile terminal intended to be received in the accommodation,
a portable piece of equipment attached to the user comprising a support designed to be adjusted to the head of the user and an arm mounted on the support and carrying at its distal end a first video camera, in an axis of gaze of the user, and a first light source directed toward the eye and situated near to an objective lens of the first video camera, and a processing unit comprising a first video input interface capable of receiving a first video signal captured by the first video camera of the portable equipment comprising an image of the pupil, that of a corneal reflection of the first light source directed toward the eye and that of corneal reflections corresponding to each of the reference light sources equipping the device for supporting the mobile terminal, a second video input interface capable of receiving a second video signal comprising an image of the display surface being observed by the user, and a processor module capable of measuring, from the first video signal, the direction of gaze in the reference frame of the eye as a function of the position of the center of the pupil with respect to the center of the corneal reflection of the first light source and of determining the position of the gaze in the plane of the display surface being observed, based on the position of the center of the corneal reflections of the reference light sources in the first video signal and on the direction of gaze measured in the reference frame of the eye.

8. The system as claimed in claim 7, wherein the device comprises a first support frame designed for holding the plurality of reference light sources, the first support frame being composed of a plurality of arms mounted on the supporting element at a respective first end of each of them and on a respective second end of which a respective light source from the plurality of reference light sources is mounted.

9. The system as claimed in claim 7, wherein the device comprises furthermore a second video camera attached to the supporting element and capable of being oriented toward the accommodation designed to receive the mobile terminal for capturing images of the display surface being observed.

10. The system as claimed in claim 9, further comprising a second support frame designed to support the second video camera, comprising an arm attached by a first end to the supporting element, and extending from this first end to a second end positioned above the accommodation designed to receive the mobile terminal, this second end of the arm being equipped with means for fixing the video camera capable of holding the video camera in the correct orientation.

11. The system as claimed in claim 7, wherein the plurality of reference light sources is composed of four light-emitting diodes non-aligned when they are taken in threes.

12. The system as claimed in claim 11, wherein the light-emitting diodes emit radiation in the infrared wavelength range.

13. The system as claimed in claim 7, wherein the tray is mounted in rotation on the supporting element between at least two positions substantially at a right angle to each other, in such a manner as to respectively define a position referred to as portrait and a position referred to as landscape for the display surface of the mobile terminal intended to be received in the accommodation, and said device comprises locking means for the tray in each of these respective positions.

14. The system as claimed in claim 7, wherein the device for supporting the mobile terminal comprises a second video camera for supplying the second video signal, the second video camera being attached to the supporting element of the device for supporting the mobile terminal and being capable of being oriented toward the accommodation designed to receive the mobile terminal in order to capture images of the display surface being observed, and in that the second video input interface of the processing unit is connected to a video output of the second video camera.

15. The system as claimed in claim 7, wherein the second video input interface of the processing unit is connected to a video output of the mobile terminal capable of supplying the second video signal.

16. The system as claimed in claim 7, wherein the processing unit comprises a video output interface capable of supplying the second video signal in which the images of the display surface being observed display a cursor representing the position of the gaze in the plane of the surface being observed determined by the processor module.

17. The system as claimed in claim 7, further comprising a module for synchronizing the illumination of the first light source and of the reference light sources with the capture of the first video signal by the first video camera of the portable equipment, said synchronization module comprising a video input interface capable of receiving the first video signal from the first video camera of the portable equipment, power supply means designed to control in a synchronous manner the illumination and the extinction of the first light source and of the reference light sources and means for processing the received video signal configured with said power supply means so as to control the illumination of the first light source and of the reference light sources at the rate of one image in two with respect to the images captured by the first video camera of the portable equipment.

18. The system as claimed in claim 7, wherein the arm mounted onto the support of the portable equipment is a telescopic arm equipped with anti-rotation means for maintaining the first video camera in the correct orientation.

19. The system as claimed in claim 18, wherein the telescopic arm comprises linked sliding parallel rods, at least one of which has a sliding control at the proximal end of the arm.

20. The system as claimed in claim 7, wherein the support of the portable equipment is a spectacle frame with two branches, the arm being fixed onto one of the branches of the frame.

21. The system as claimed in claim 7, wherein the arms mounted on the support of the portable equipment carry a second light source directed toward the eye near to the objective lens of the first video camera and designed to promote the illumination of the eye.

\* \* \* \* \*